United States Patent
Luecke et al.

(10) Patent No.: US 8,837,043 B2
(45) Date of Patent: Sep. 16, 2014

(54) LIGHT SOURCE ARRANGEMENT FOR AN ILLUMINATION DEVICE OF A MEDICAL-OPTICAL OBSERVATION APPARATUS

(75) Inventors: Christian Luecke, Oberkochen (DE); Markus Bausewein, Aalen (DE); Peter Reimer, Ellwangen (DE)

(73) Assignee: Carl Zeiss Meditec AG (DE)

( * ) Notice: Subject to any disclaimer, the term of this patent is extended or adjusted under 35 U.S.C. 154(b) by 286 days.

(21) Appl. No.: 12/796,253

(22) Filed: Jun. 8, 2010

(65) Prior Publication Data

US 2010/0309549 A1   Dec. 9, 2010

(30) Foreign Application Priority Data

Jun. 9, 2009   (DE) .......................... 10 2009 024 942

(51) Int. Cl.
  *G02B 21/06*   (2006.01)
(52) U.S. Cl.
  USPC ........................................ 359/385; 359/432
(58) Field of Classification Search
  USPC ................... 359/385, 432, 386–390
  See application file for complete search history.

(56) References Cited

U.S. PATENT DOCUMENTS

| | | | |
|---|---|---|---|
| 5,777,784 A * | 7/1998 | Tanaka ........................... | 359/388 |
| 5,914,771 A | 6/1999 | Biber | |
| 5,973,829 A | 10/1999 | Moeller et al. | |
| 6,011,647 A | 1/2000 | Geschwentner | |
| 6,939,006 B2 | 9/2005 | Goldfain et al. | |
| 7,347,552 B2 | 3/2008 | Reis | |
| 7,599,115 B2 * | 10/2009 | Gugel ........................... | 359/385 |
| 2003/0112505 A1 | 6/2003 | Nihoshi | |
| 2005/0046937 A1 | 3/2005 | Sander | |
| 2005/0128574 A1 | 6/2005 | Reimer et al. | |
| 2006/0198001 A1 | 9/2006 | Spink | |
| 2008/0297892 A1 | 12/2008 | Abele et al. | |
| 2009/0059359 A1 | 3/2009 | Nahm et al. | |
| 2009/0273757 A1 | 11/2009 | Merz et al. | |

FOREIGN PATENT DOCUMENTS

| | | |
|---|---|---|
| DE | 16004 | 4/1914 |
| DE | 196 38 263 | 4/1998 |
| DE | 20 2004 019 849 | 3/2005 |
| DE | 2004 019 849 | 3/2005 |
| DE | 103 47 732 | 5/2005 |
| DE | 699 19 902 | 9/2005 |
| DE | 10 2005 032 501 | 3/2006 |
| DE | 10 2006 013 761 | 9/2007 |
| DE | 102006047724 | 2/2008 |
| DE | 10 2007 041 003 | 12/2008 |
| DE | 10 2007 041 439 | 3/2009 |
| EP | 0 661 020 | 7/1995 |
| JP | 01164351 | 6/1989 |
| JP | 2002010978 | 1/2002 |

* cited by examiner

*Primary Examiner* — Frank Font
(74) *Attorney, Agent, or Firm* — Gerald E. Hespos; Michael J. Porco; Matthew T. Hespos

(57) ABSTRACT

A light source arrangement (101) for an illumination device of a medical-optical observation apparatus has an illumination light source (7) and an illumination optical unit (15) for illuminating an observation object (23) with illumination light from the illumination light source (7). The light source arrangement (101) has at least one luminescence emitter (3) as light source and an imaging optical unit (105) that generates an image (7) of the at least one luminescence emitter (3) with a defined magnification scale, which image forms the illumination light source for the illumination device.

13 Claims, 4 Drawing Sheets

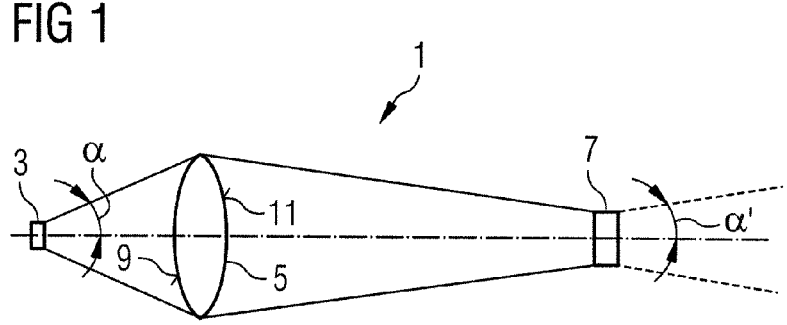
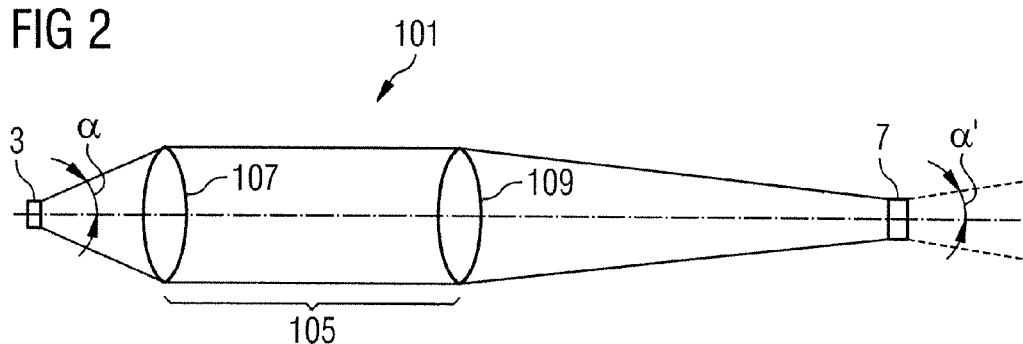
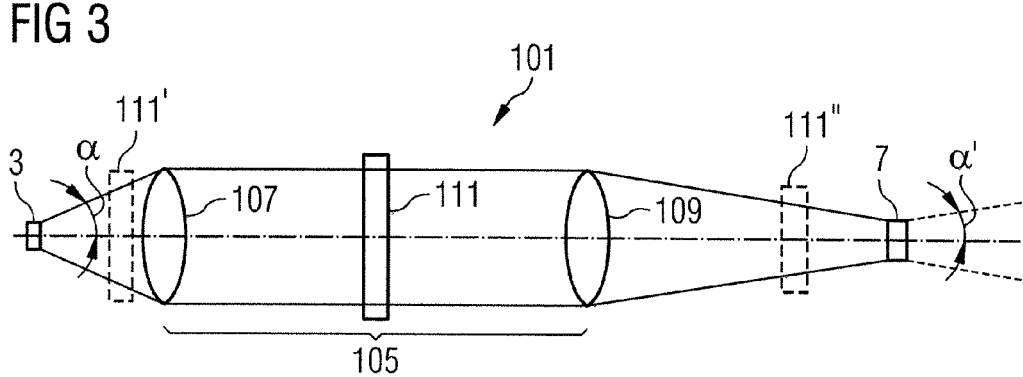

LIGHT SOURCE ARRANGEMENT FOR AN ILLUMINATION DEVICE OF A MEDICAL-OPTICAL OBSERVATION APPARATUS

BACKGROUND OF THE INVENTION

1. Field of the Invention

The present invention relates to a light source arrangement for an illumination device of a medical-optical observation apparatus, which illumination device has an illumination light source and an illumination optical unit for illuminating an observation object with illumination light from the illumination light source. The invention additionally relates to an illumination device for a medical-optical observation apparatus, and such a medical-optical observation apparatus.

2. Description of the Related Art

An illumination device for a surgical microscope, embodied as an ophthalmological surgical microscope, is described for example in DE 10 2007 041 003 A1, wherein the illumination systems in the surgical microscope are supplied from a halogen or xenon light source via spliced optical waveguides. This means, however, that the illumination types of coaxial illumination and surrounding illumination cannot be regulated independently of one another. In the case where a plurality of optical waveguides are used, although separate regulation is possible in principle, this increases the complexity of the illumination system.

DE 20 2004 019 849 U1 and EP 0 661 020 A1 additionally disclose illumination devices which provide separate light sources for red reflection illumination and surrounding illumination. DE 20 2004 019 849 U1 additionally mentions that light emitting diodes can be used as the light source. However, no further explanation is given regarding the practical configuration of the illumination device when using light emitting diodes as light sources.

It is an object of the present invention to provide an advantageous light source arrangement for an illumination device of a medical-optical observation apparatus. It is a further object of the present invention to provide an advantageous illumination device for a medical-optical observation apparatus. Finally, it is an object of the present invention to provide an advantageous medical-optical observation apparatus.

SUMMARY OF THE INVENTION

The invention provides a light source arrangement for an illumination device of a medical-optical observation apparatus, the illumination device having an illumination light source and an illumination optical unit for illuminating an observation object with illumination light from the illumination light source. The light source arrangement comprises at least luminescence emitters as primary light source for the illumination device. The light source arrangement furthermore comprises an imaging optical unit, which generates an image, in particular a real image, of the at least one luminescence emitter with a defined magnification scale. The image constitutes the illumination light source for the illumination device. In the simplest case, a converging lens can be employed as imaging optical unit. However, more complex optical units can preferably be used as well.

The present invention is based on the insight that, in illumination devices for medical-optical observation apparatuses, the light sources used heretofore, such as exit ends of optical fibers, incandescent lamps or gas discharge lamps, cannot be replaced by a light emitting diode without either bringing about a loss in quality of the illumination or adapting the illumination optical unit of the illumination device to the new light source. By way of example, in the case of an illumination device having the exit end of an optical fiber as illumination light source, the replacement of the exit end by a light emitting diode would lead, on account of the different emission characteristics, to a significant reduction of the quantity of illumination light transmitted via the illumination optical unit if the illumination optical unit were not adapted to the new light source. However, since a light emitting diode has a significantly larger emission angle than the exit end of an optical fiber, the illumination optical unit would have to be configured with a larger numerical entrance aperture, which would enlarge the optical components in terms of their diameter. Such enlargement means more structural space, however, which would make the illumination device more bulky. Moreover, it is not readily possible to replace the optical components in existing illumination devices. According to the invention, therefore, the light emitting diode itself is not used as the illumination light source, rather an image of the illumination light source is used, which image is generated by means of an imaging optical unit with a defined magnification scale. The image of the at least one luminescence emitter can thus be optimally adapted to the illumination optical unit of the illumination device.

In the abovementioned example with the exit end of an optical fiber and the LED, the following conditions are present: the emission angle of an optical fiber is approximately ±34°. By contrast, the emission angle of a light emitting diode, which is a luminescence emitter that is particularly suitable as a light source, is ±60°, that is to say almost double that of the optical fiber. However, the illumination optical unit of the illumination device is adapted to the transmission of illumination light with an aperture angle such as is offered by the optical fiber. In the light source arrangement according to the invention, then, the imaging optical unit can be designed in such a way that the imaging scale of the image of the light emitting diode is approximately 2×. As a result, the luminous area of the image is increased by a factor of 2 by comparison with the original light emitting diode, and at the same time the emission angle is reduced by a factor of 2. Therefore, the emission angle is approximately ±30°, which approximately corresponds to the emission angle of an optical fiber. In this case, the luminous area of the light emitting diode can be chosen such that the image of the luminous area magnified by a factor of 2 corresponds approximately to the luminous area of the exit end of an optical fiber. If the light source arrangement according to the invention is then arranged in relation to the illumination device such that the image of the light emitting diode enlarged by a factor of 2 is situated where the exit end of the optical fiber would otherwise be situated, the light of the light emitting diode, that is to say the light of the image thereof, can be coupled into the illumination optical unit adapted to the optical fiber just as well as the light from the optical fiber itself. The adaptation to the emission characteristic of an incandescent lamp or of a gas discharge lamp can also be effected in a similar manner. The light source arrangement according to the invention can therefore be used with existing illumination devices without an adaptation to the new light source having to be performed in the case of said existing illumination devices.

A double collector can advantageously be employed as the imaging optical unit. Such a double collector affords the possibility that a parallel beam path is present between the two lenses of the double collector. In this way, the image of the at least one luminescence emitter can be generated at any desired distance from the luminescence emitter. With the use of light-directing elements such as, for instance, mirrors or prisms, great freedom then arises in the positioning of the at least one luminescence emitter. The latter can therefore also be arranged at a greater distance from the illumination device. Moreover, a total of at least four lens surfaces are then available, which can be chosen in a suitable manner for producing an optimized imaging quality.

In one development of the invention, the imaging optical unit of the light source arrangement has at least one aspherical lens, which can be advantageous with regard to the correction of imaging aberrations, particularly with regard to the correction of a spherical aberration. Moreover, the imaging optical unit can comprise an achromatic or apochromatic lens in order that chromatic aberrations in the imaging of the luminescence emitter are kept small. This is advantageous, in particular, if a luminescence emitter that emits broadband light such as, for instance, a white light emitting diode is employed. Instead of a luminescence emitter that emits broadband light, however, it is also possible to employ a luminescence emitter that emits narrowband light, for example if illumination in a narrow spectral range is intended to be effected. However, a luminescence emitter that emits narrowband light can also be employed if the illumination of an observation object with broadband light is intended to be effected. In this case, the light source arrangement comprises a converter element, that is to say an independent part not integrated into the luminescence emitter, which converter element is provided with a converter phosphor for converting at least part of the narrowband light of the luminescence emitter. In that case the converter element is introduced or can be introduced into the light source arrangement between the at least one luminescence emitter and the image of the at least one luminescence emitter, for example between the imaging optical unit and the image of the at least one luminescence emitter. In such a configuration of the light source arrangement, by exchanging the converter element for a converter element having a different converter phosphor, it is possible to alter the spectral characteristic of the image of the light source, for example in order to provide light having a specific color temperature.

The converter element can have an entrance surface for the light emerging from the luminescence emitter, which entrance surface faces the luminescence emitter and is provided with a dichroic layer that is transparent to light entering into the converter element and having the wavelength distribution of the light emitted by the luminescence emitter. By contrast, said dichroic layer is highly reflective to converted light directed in the direction of the luminescence emitter. In this way, it is possible to prevent converted light from emerging from the converter element in the direction of the luminescence emitter and thus being lost for the illumination.

An illumination device according to the invention for a medical-optical observation apparatus is equipped with at least one light source arrangement according to the invention. The use of a light source arrangement according to the invention with a luminescence emitter, for instance an LED, as primary light source affords a considerable price advantage, and additionally a longer service life, compared with the use of halogen and xenon lamps. In comparison with the use of an optical fiber as a light source, light emitting diodes, in particular, afford the advantage of more homogeneous light propagation.

If the illumination device has at least two illumination light sources, the latter can be formed, in particular, by the same light source arrangement. In other words, the light source arrangement then comprises at least two luminescence emitters that are imaged by means of the same imaging optical unit. As an alternative, however, there is also the possibility of using two separate light source arrangements as illumination light sources. In other words, at least two light source arrangements each having a dedicated luminescence emitter and a dedicated imaging optical unit can be employed.

A medical-optical observation apparatus according to the invention, which can be embodied for example as an endoscope or in particular as a surgical microscope, is equipped with an illumination device according to the invention. The advantages that can be obtained in this case are apparent from the advantages that have already been described with regard to the illumination device according to the invention and with regard to the light source arrangement according to the invention.

Further features, properties and advantages of the invention will become apparent from the following description of exemplary embodiments with reference to the accompanying figures.

BRIEF DESCRIPTION OF THE DRAWINGS

FIG. 1 shows a first exemplary embodiment of a light source device according to the invention.

FIG. 2 shows a second exemplary embodiment of a light source device according to the invention.

FIG. 3 shows a third exemplary embodiment of a light source device according to the invention.

DETAILED DESCRIPTION OF THE PREFERRED EMBODIMENTS

Figure 4:
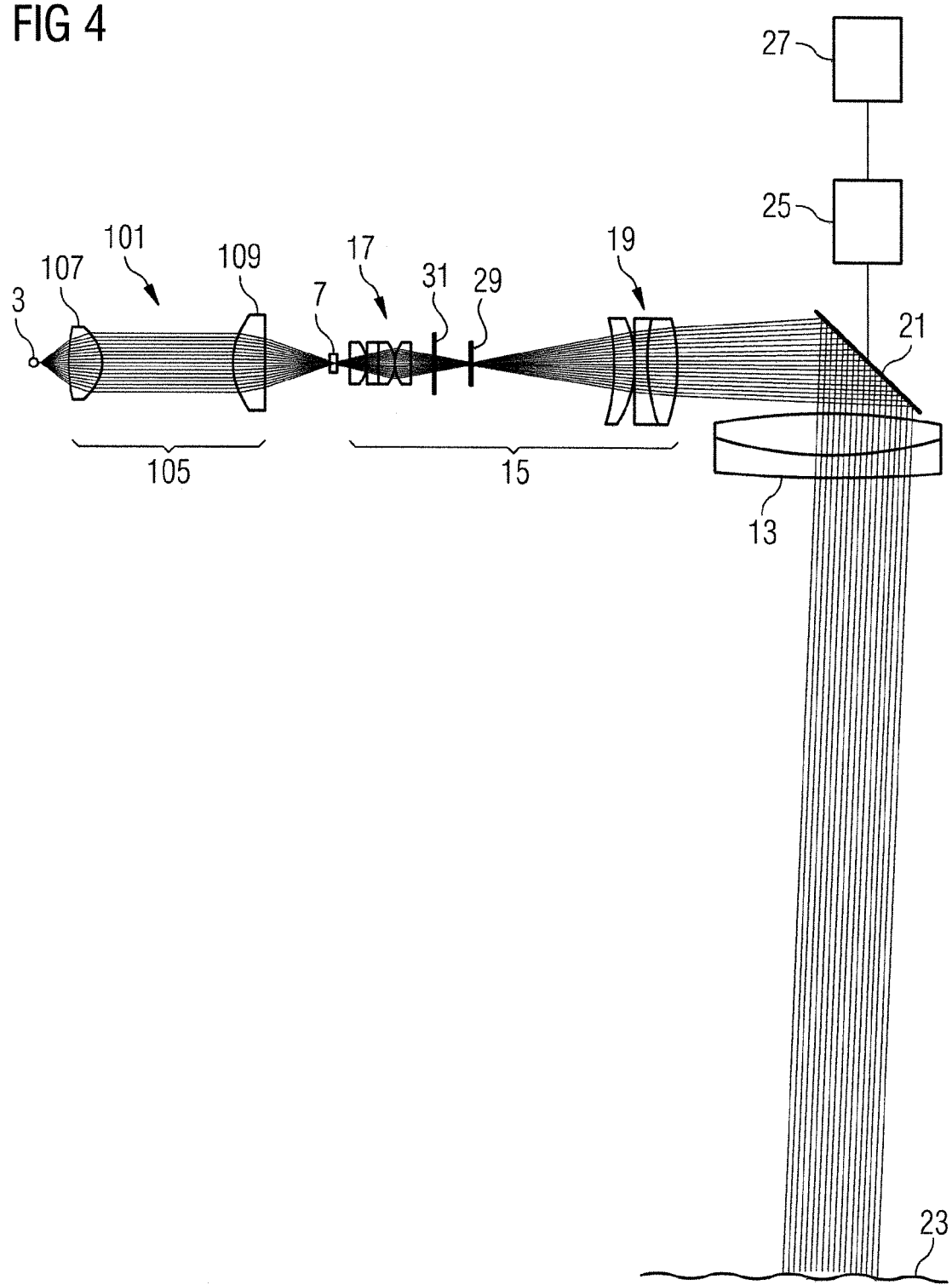
FIG. 4 shows a first exemplary embodiment of a medical-optical observation apparatus comprising an illumination device according to the invention.

A first exemplary embodiment of a light source arrangement according to the invention is described below with reference to FIG. 1. The figure shows the simplest construction of the light source arrangement 1 according to the invention, comprising merely a luminescence emitter, a light emitting diode 3 in the present exemplary embodiment, as primary light source and a converging lens 5. The converging lens 5 constitutes the imaging optical unit of the light source arrangement, with the aid of which a real image 7 of the light emitting diode 3 is generated. The optical parameters of the converging lens 5, that is to say its refractive index and the curvatures of the lens surfaces are chosen such that the magnification scale of the image 7 in comparison with the light emitting diode 3 as the original image lies between 1.5 and 2.5, and in particular between 2 and 2.5. This has the effect that the luminous area of the image 7 is 1.5 times to 2.5 times as large as the luminous area of the light emitting diode 3, and in particular 2 times to 2.5 times as large. In the present exemplary embodiment, the magnification scale is 2, that is to say the aperture angle $\alpha$ of the radiation beam emitted by the light emitting diode 3 is twice as large as the aperture angle $\alpha'$ of the radiation beam emerging from the image 7. In addition, the luminous area of the image 7 is twice as large as the luminous area of the light emitting diode 3.

If it is assumed that a light emitting diode emits with an aperture angle of around ±60°, the aperture angle $\alpha'$ with which the image 7 of the light emitting diode emits is ±30°, which corresponds approximately to the emission angle of the exit end of an optical fiber. In the case of a light source arrangement having a magnification scale of approximately 2, therefore, the image 7 of the light emitting diode 3 can be arranged instead of the exit end of an optical fiber in an illumination device for a medical-optical observation apparatus.

A second exemplary embodiment of the light source arrangement according to the invention is illustrated in FIG. 2. Elements which do not differ from the first exemplary embodiment are designated by the same reference signs as in FIG. 1 and will not be explained again.

The light source arrangement in accordance with the second exemplary embodiment illustrated in FIG. 2 differs from the light source arrangement illustrated in FIG. 1 in that the imaging optical unit 105 is embodied in the form of a double collector having two converging lens 107, 109. The imaging optical unit 105 generates an image 7 of the light emitting diode 3 with an imaging scale of approximately two. However, other imaging scales, in particular imaging scales between 1.5 and 2.5, and in particular between 2 and 2.5 are also possible.

The lenses of the double collector 105, which are illustrated only schematically in FIG. 2, can be double-convex and/or planoconvex lenses having spherical and/or aspherical lens surfaces. The lens 107 of the double collector that is situated on the light emitting diode side is configured such that it images the light emitting diode 3 toward infinity, that is to say generates a parallel radiation beam. The latter is in turn focused by the lens 109 situated on the image side, in order to generate the image 7 of the light emitting diode 3.

Since a parallel radiation beam is present between the two lenses 107, 109 of the double collector, the distance between the two lenses 107, 109 can be varied and afocal optical elements, for example mirrors or prisms for deflecting the radiation beam, can additionally be arranged therebetween. Great freedom between the arrangement of the light emitting diode 3 as luminescence emitter and the image 7 of the light emitting diode 3 is achieved in this way.

In the first exemplary embodiment as also in the second exemplary embodiment, white light emitting diodes are employed as broadband luminescence emitters. However, there is also the possibility of using narrowband luminescence emitters, for example blue or red light emitting diodes, instead of broadband luminescence emitters. Depending on the medical-optical apparatus for which the light source arrangement is intended to be used, it is also possible to use luminescence emitters which emit in the non-visible spectral range, for example light emitting diodes which emit in the ultraviolet or infrared spectral range. This can be expedient, for instance, if fluorescence is intended to be excited in the observation object by means of the light source arrangement.

However, even if the observation object is intended to be illuminated with white illumination light, it is possible to employ a narrowband luminescence emitter, for example a blue light emitting diode or a light emitting diode which emits in the ultraviolet spectral range. In order nevertheless to be able to provide broadband illumination light, in particular white illumination light, the light source arrangement is then equipped with a converter element, which converts at least part of the light emitted by the light emitting diode into light having a longer wavelength.

A light source arrangement comprising a converter element is illustrated in FIG. 3. The basic construction of the light source arrangement illustrated in FIG. 3 corresponds to that of the light source arrangement illustrated in FIG. 2. There is just a converter element 111 arranged between the two converging lenses 107, 109 of the double collector 105. In principle, however, the converter element 111 can also be arranged between the light emitting diode 3 and the lens 107 on the light emitting diode side, or between the lens 109 on the image side and the image 7, as is indicated by the reference signs 111' and 111" in FIG. 3. In the last-mentioned case, in particular, it is possible to avoid chromatic aberrations even without achromatic or apochromatic lenses since the imaging optical unit 105 is only permeated by a narrow wavelength distribution.

The converter element 111 is equipped with a converter phosphor that converts at least a portion of the narrowband light from the light emitting diode 3 into light having a longer wavelength. If the light emitting diode 3 emits blue light, for example, the converter phosphor can be chosen such that it converts part of the blue light into yellow light, such that the superimposition of the yellow light with the remaining blue light produces white light. By contrast, if a light emitting diode which emits UV radiation is used, for example, it is possible to convert the UV radiation completely into light in the visible spectral range by means of the converter phosphor. In addition, it is possible by using a plurality of converter elements which are introduced or can be introduced one behind another in the light source arrangement and have different converter phosphors, or by means of one converter element comprising a converter phosphor mixture, to convert the UV radiation completely into light having at least two wavelength distributions that in total result in the broadband or white light. However, the use of converter elements which are arranged in the light source arrangement or can be introduced into the light source arrangement one behind another or of one converter element which is arranged in the light source arrangement or can be introduced into the light source arrangement with a phosphor mixture is possible, in principle, not only with the use of an LED which emits in the UV range, but also with the use of an LED which emits in the visible spectral range.

Particularly if the converter element or the converter elements of the light source arrangement is or are configured in exchangeable fashion, the spectral wavelength distribution of the light emitted by the image 7 can be set in wide ranges, for example in order to be able to realize white light having different color temperatures and/or light having white and non-white wave distributions.

In order to increase the efficiency of the converter element z the latter can be provided with a dichroic layer at its surface facing the light emitting diode, said dichroic layer being transmissive to the light from the light emitting diode but highly effective for converted light.

A surgical microscope as an example of a medical-optical observation apparatus having an illumination device which comprises a light source arrangement according to the invention is illustrated in a schematic side view in FIG. 4. Besides a light source arrangement 101 according to the invention, the construction of which substantially corresponds to that of the light source arrangement described in FIG. 2, the figure shows the main objective 13 of the surgical microscope and also an illumination optical unit 15, which comprises a collector optical unit 17 and a condenser optical unit 19. In the present exemplary embodiment, both the collector optical unit 17 and the condenser optical unit 19 are constructed from lens groups in order to reduce imaging aberrations in the illumination beam path as far as possible. By means of a beam splitter, for example a partly transmissive mirror 21, the illumination beam path is coupled into the main objective 13 and fed to the observation object 23 via the main objective.

The light source device 101 comprises aspherical lens surfaces in FIG. 4 in order to minimize imaging aberrations in the image 7 of the light emitting diode 3.

Besides the illumination beam path comprising the optical elements of collector 17, condenser 19, beam splitter 21 and main objective 13, the surgical microscope has an observation beam path. The latter, proceeding from the observation object 23, runs through the main objective 13 and the beam splitter 21, wherein the observation beam path, in contrast to the illumination beam path, is not deflected by the beam splitter 21. In the observation beam path, the beam splitter 21 is followed by a magnification setting element 25, by means of which the magnification factor with which a magnification is effected in the observation beam path can be set. The magnification setting element 25 can be embodied, in particular, as a zoom system containing at least three lenses or lens groups, wherein two lenses or lens groups can be displaced along the optical axis, such that the magnification factor can be set in a continuously variable fashion. As an alternative, it is also possible for the magnification setting element 25 to be configured as a stepped magnification changer. An element of the latter type contains a plurality of lens groups, wherein the lenses of a lens group are in a fixedly predefined arrangement with respect to one another. In such a stepped magnification changer, the magnification factor is changed by different lens groups of this type being alternately introduced into the observation beam path.

The magnification setting unit 25 can already be embodied as a two-channel optical unit, that is to say that it has a left and a right stereoscopic partial beam path, wherein each partial beam path has its own optical elements. As an alternative, however, the magnification setting unit can also be embodied as a so-called "large optical unit", that is to say that its optical elements are so large that they are simultaneously permeated by both stereoscopic partial beam paths.

The magnification setting unit 25 is then followed by a purely optical or an optical/electronic binocular tube 27. In a purely optical binocular tube 27, a tube objective and an eyepiece are arranged in each stereoscopic partial beam path. By means of the tube objectives, intermediate images are respectively generated in the stereoscopic partial beam paths, said intermediate images being imaged toward infinity by means of the eyepiece optical unit, such that an observer can observe the intermediate images with a relaxed eye. In a combined optical and electronic binocular tube 27, each stereoscopic partial beam path contains an imaging optical unit that images the observation object 23 onto two electronic image sensors.

In the present exemplary embodiment, the illumination device of the surgical microscope is embodied as so-called Köhler illumination. In such illumination, the light source, that is to say the image 7 of the light emitting diode 3, is imaged into an intermediate image plane, in which, in general, an aperture diaphragm 29 is situated, with the aid of which the brightness of the illumination can be set in a targeted manner. A luminous field diaphragm 31 is furthermore present, which is situated in the observation beam path in a conjugate plane with respect to the object plane of the observation object 23. Objects arranged in such a conjugate plane are sharply imaged in the object plane. By means of the luminous field diaphragm 31, therefore, it is possible to realize a sharp delimitation of the luminous field in the object. Overall, with a Köhler optical unit, it is possible to generate a sharply delimited homogeneous luminous field in the object 23. The illumination optical unit illustrated in FIG. 4 substantially corresponds to the illumination optical unit described in DE 10 2006 013 761 A1 with the difference that, instead of the optical fiber exit end described therein, the image 7 of the light emitting diode 3 serves as a light source.

Figure 5:
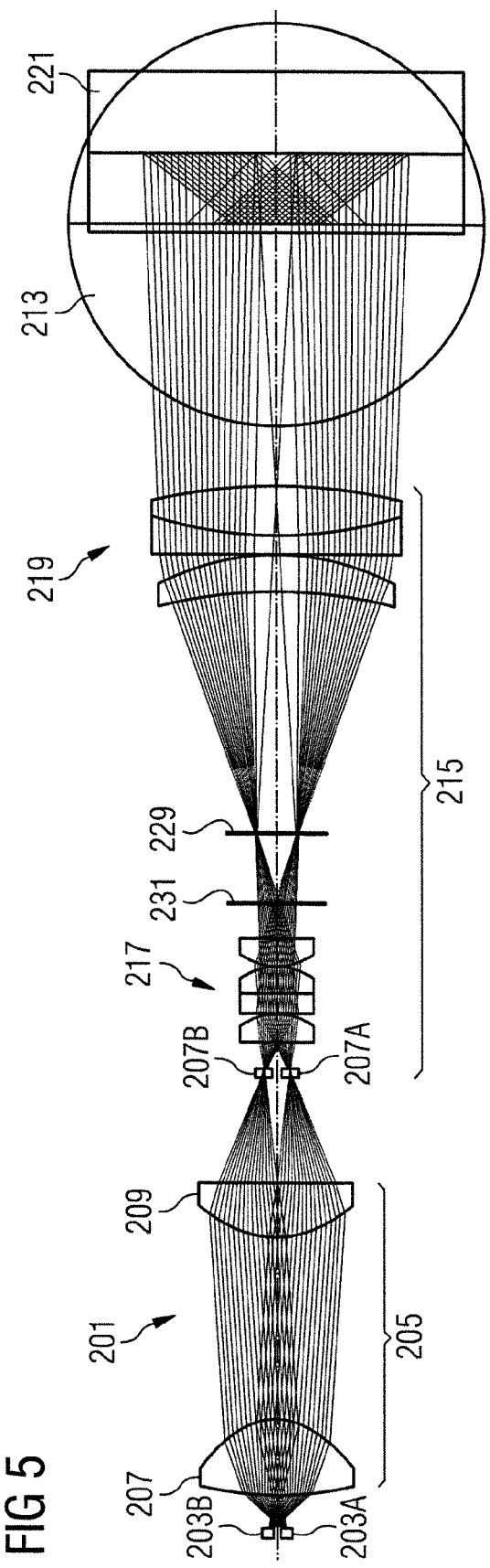
FIG. 5 shows a second exemplary embodiment of a medical-optical observation apparatus comprising an illumination device according to the invention.

FIG. 5 shows a modification of the surgical microscope illustrated in FIG. 4, in a plan view. The exemplary embodiment illustrated in FIG. 5 differs from the exemplary embodiment illustrated in FIG. 1 both in terms of the light source arrangement 201 and in terms of the illumination optical unit 215 in that it is embodied for realizing a coaxial illumination. In such a coaxial illumination, the illumination comprises two partial illumination beam paths, which are fed to the object by means of a beam splitter 221 coaxially with respect to the stereoscopic partial observation beam paths.

In the exemplary embodiment illustrated in FIG. 5, the light source arrangement 201, for generating the coaxial illumination comprises two luminescence emitters, namely two light emitting diodes 203A, 203B, and also a double collector 205 having two converging lenses 207, 209, which are embodied as large lenses, that is to say that the lenses are permeated both by the light emerging from the light emitting diode 203A and by the light emerging from the light emitting diode 203B, in order to generate images 207A, 207B of the light emitting diodes. The lens surfaces are aspherical in order to make it possible to generate the two images with the smallest possible imaging aberrations. The distance between the two images 207A, 207B is enlarged like the luminous area and the emission angle with the magnification scale of the imaging optical unit, such that a suitable distance between the two images 207A, 207B can be realized by suitable setting of the distance between the two light emitting diodes 203A, 203B.

The illumination optical unit 215 is likewise embodied as a large optical unit, that is to say that a common collector optical unit 217 and a common condenser optical unit 219 are in each case present both for the beam path emerging from the image 207A and for the beam path emerging from the image 207B. Only the aperture diaphragm 229 situated in the intermediate image plane of the illumination optical unit 215 and the luminous field diaphragm 231 situated in the conjugate plane with respect to the object plane are equipped as double diaphragms, that is to say that they respectively have a diaphragm opening for each partial beam path of the illumination.

By means of the beam splitter 221 the two partial beam paths of the observation optical unit are then deflected through the main objective 213 in the direction of the observation object. Such coaxial illumination is often employed in ophthalmological surgical microscopes, for example, for the purpose of generating red reflection illumination.

Figure 6:
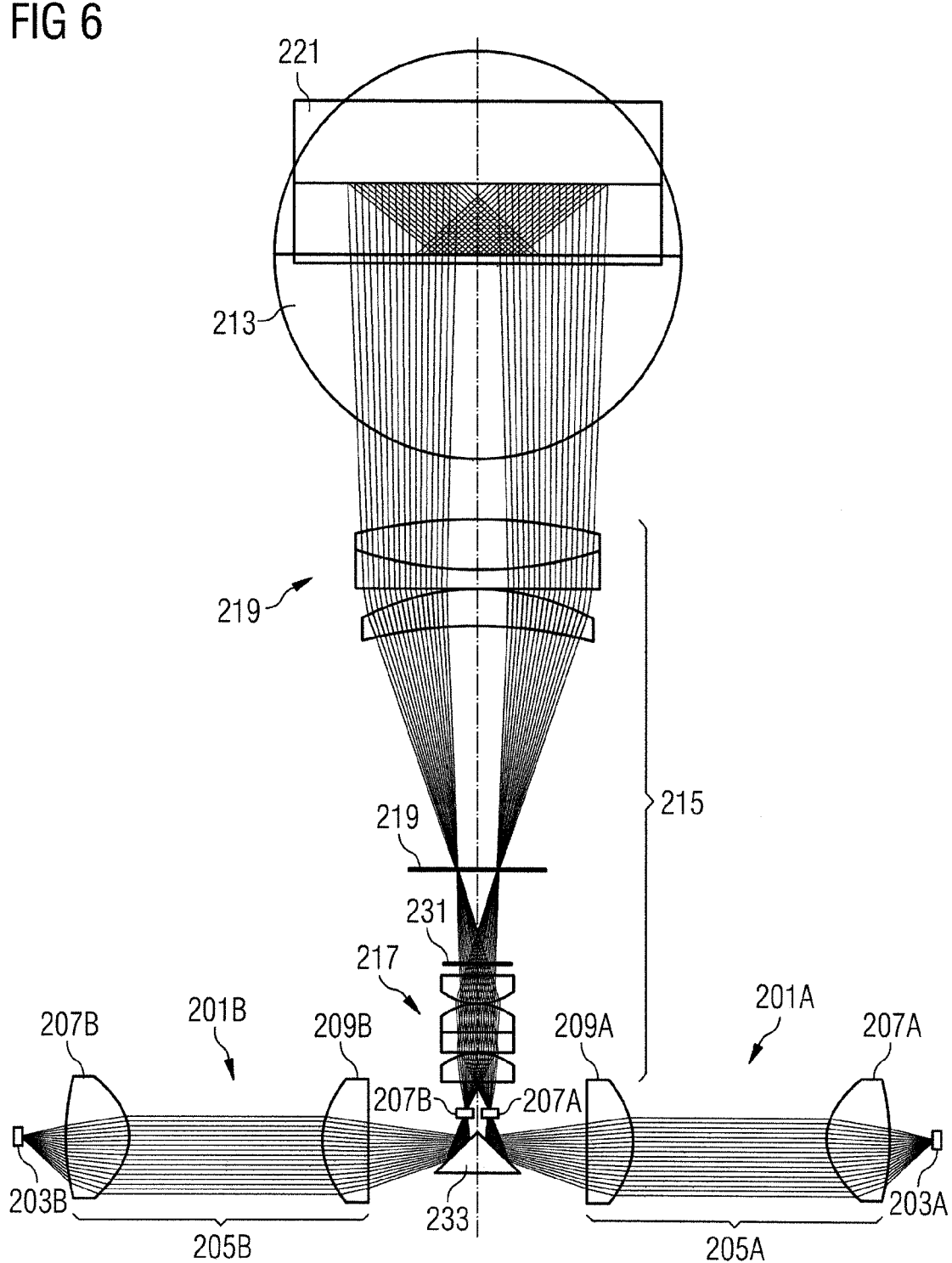
FIG. 6 shows a third exemplary embodiment of a medical-optical observation apparatus comprising an illumination device according to the invention.

An alternative realization of the coaxial illumination is illustrated in a plan view in FIG. 6. The illumination device 215 and also the beam splitter 221 and the main objective 213 do not differ from the corresponding elements from FIG. 5 and are therefore designated by the same reference signs as in FIG. 5.

The modification shown in FIG. 6 differs from the surgical microscope illustrated in FIG. 5 in that, instead of a light source arrangement 201 comprising two luminescence emitters 203A, 203B, two light source arrangements 201A, 201B are employed, each comprising a single luminescence emitter 203A, 203B in the form of light emitting diodes. Each luminescence emitter 203A, 203B is assigned a dedicated imaging optical unit 205A, 205B, which in each case corresponds to the imaging optical unit 105 shown in FIG. 4.

In the exemplary embodiment illustrated, the two light source arrangements 201A, 201B are arranged opposite one another at an angle of 90° with respect to the optical axis of the illumination optical unit 215, that is to say that the optical axes of the double collectors 205A, 205B of the two light source arrangements 201A, 201B are at an angle of 90° with respect to the optical axis of the illumination optical unit 215. By means of a triangular mirror 233, the two radiation beams of the light source arrangements are deflected by 90° in order that the images 207A, 207B of the light emitting diodes 203A, 203B, can be coupled into the illumination optical unit 215.

Although the optical axes of the light source arrangements 201A, 201B in FIG. 6 are at an angle of 90° with respect to the optical axis of the illumination optical unit 215, the light source arrangements 201A, 201B can also be arranged at a different angle relative to the optical axis of the illumination optical unit 215. The angle of the triangular mirror 233 should then be adapted accordingly.

While the variant illustrated in FIG. 5 with a single light source arrangement comprising two light emitting diodes affords the advantage that only a single double collector has to be present, the variant illustrated in FIG. 6 affords the possibility of using standard light emitting diodes in each light source arrangement 201A, 201B. In the variant illustrated in FIG. 5, by contrast, under certain circumstances, a special production of the two LEDs 203A, 203B is necessary in order to bring their luminous areas close enough to one another in order that the distance between the images 207A, 207B does not become too large for the desired application.

The invention has been described on the basis of specific exemplary embodiments for explanation purposes. However, it is possible to depart from these exemplary embodiments. Thus, mirrors or prisms can be present between the two lenses of the double collector, for example, in order to fold the beam path. The structural length of the light source arrangement can thereby be shortened.

The light source arrangement according to the invention makes it possible to use luminescence emitters such as, in particular, light emitting diodes, but also organic light emitting diodes or luminescence films, provided that the intensity thereof is high enough, instead of incandescent lamps or gas discharge lamps as primary light sources. Through a suitable choice of the imaging optical unit it is possible to generate images of the luminescence emitters which can then be used as an illumination light source of the illumination optical unit in a medical-optical observation apparatus. By comparison with the use of incandescent lamps or gas discharge lamps, this results in price advantages and also a longer service life. The light source arrangement according to the invention affords more homogeneous light propagation by comparison with the output ends of optical fibers as illumination light sources.

What is claimed is:

1. An illumination device for medical-optical observation apparatus comprising:
    an illumination optical unit with a collector optical unit (17, 217) forming an entry end for receiving light from an illumination light source, a condenser optical unit (19, 219) forming an exit end for illuminating an observation object (23) with illumination light from the illumination light source (7, 207) and an aperture diaphragm (29, 229) located between the collector optical unit (17, 217) and the condenser optical unit (19, 219); and
    at least one light source arrangement (101, 201) having at least one luminescence emitter (3, 203) as primary light source and an imaging optical unit (5, 105, 205) wherein the light source arrangement (101, 201) is located in front of the collector optical unit (17, 217) of the illumination optical unit such that the imaging optical unit (5, 105, 205) of the light source arrangement (101, 201) generates an image (7, 207) of the at least one luminescence emitter (3, 203) with a defined magnification scale at a distance from the aperture diaphragm (29, 229) and between the imaging optical unit (5, 105, 205) of the light source arrangement (101, 201) and the collector optical unit (17, 217) of the illumination optical unit, and wherein the image (7, 207) with the defined magnification scale forms the illumination light source for the illumination optical unit.

2. The illumination device of claim 1, wherein the imaging optical unit is a double collector (105, 205).

3. The illumination device of claim 1, wherein the imaging optical unit (5, 105, 205) has at least one aspherical lens.

4. The illumination device of claim 1, wherein the imaging optical unit (5, 105, 205) comprises an achromatic or apochromatic lens.

5. The illumination device of claim 1, wherein the luminescence emitter emits broadband light.

6. The illumination device of claim 1, wherein the luminescence emitter (3, 203) emits narrowband light.

7. The illumination device of claim 6, further comprising a converter element (111), with a converter phosphor for converting at least part of the narrowband light of the luminescence emitter (3) and introducing the narrow band light into the light source arrangement (101) between the at least one luminescence emitter (3) and the image (7) of the at least one luminescence emitter (3).

8. The illumination device of claim 7, wherein the converter element (111) is introduced into the light source arrangement (101) between the imaging optical unit and the image (7) of the at least one luminescence emitter (3).

9. The illumination device of claim 7, wherein the at least one converter element (111) has an entrance surface for the light emerging from the luminescence emitter (3), the entrance surface facing the luminescence emitter (3) and being provided with a dichroic layer that is transparent to light entering into the converter element (111) and having a wavelength distribution of the light emitted by the luminescence emitter (3) and is highly reflective to converted light directed in a direction of the luminescence emitter (3).

10. The illumination device of claim 1, wherein the image (7, 207) of the at least one luminescence emitter (3, 203) is formed with a magnification scale in the range of between 1.5× and 2.5×.

11. The illumination device of claim 1, wherein the at least one illumination light source comprises at least two illumination light sources (7A, 7B) and both illumination light sources are formed by the same light source arrangement (201).

12. The illumination device of claim 1, wherein the at least one illumination light source comprises at least two illumination light sources (7A, 7B) and each illumination light source (7A, 7B) is formed by a dedicated light source arrangement (201A, 201B).

13. A medical-optical observation apparatus comprising the illumination device of claim 1.

* * * * *